United States Patent [19]
Verbrugge et al.

[11] Patent Number: 5,874,615
[45] Date of Patent: Feb. 23, 1999

[54] METHOD FOR THE PREPARATION OF INSECTICIDAL BENZOYLUREA COMPOUNDS

[76] Inventors: Pieter Adriaan Verbrugge, Hoogaarslaan 34, 1503 WG Zaandam; Jannetje De Waal, Anjelierenstraat 25, 1131 HM Volendam, both of Netherlands

[21] Appl. No.: 40,070

[22] Filed: Mar. 17, 1998

[51] Int. Cl.$^6$ .................................................. C07C 273/18
[52] U.S. Cl. ........................... 564/44; 558/415; 546/194; 546/288; 546/291
[58] Field of Search ............................... 564/44; 558/415; 546/194, 288, 291

[56] References Cited

U.S. PATENT DOCUMENTS

| | | | |
|---|---|---|---|
| 3,748,356 | 7/1973 | Wellinga et al. | 260/553 E |
| 4,457,943 | 7/1984 | Becher et al. | 424/322 |
| 4,529,819 | 7/1985 | Clifford et al. | 564/44 |
| 4,666,942 | 5/1987 | Anderson | 514/594 |
| 4,782,090 | 11/1988 | Sirrenberg et al. | 514/584 |
| 5,157,155 | 10/1992 | Sakamoto et al. | 564/442 |

FOREIGN PATENT DOCUMENTS

| | | | |
|---|---|---|---|
| 2 165 846 | 4/1986 | United Kingdom | C07C 127/22 |
| 2 166 134 | 4/1986 | United Kingdom | C07C 127/22 |

*Primary Examiner*—Peter O'Sullivan
*Attorney, Agent, or Firm*—William H. Calnan

[57] ABSTRACT

The present invention provides an improved method for the preparation of an insecticidal benzoylurea having the structural formula I

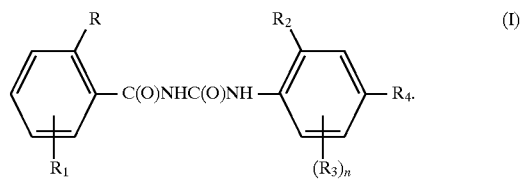

13 Claims, No Drawings

METHOD FOR THE PREPARATION OF INSECTICIDAL BENZOYLUREA COMPOUNDS

BACKGROUND OF THE INVENTION

Insecticidal benzoylureas and methods for their preparation are described in U.S. Pat. Nos. 3,748,356, 4,457,943 and 4,666,942, and UK Patent Application Nos. 2,165,846-A and 2,166,134-A, among others.

The methods described in those patents and patent applications are useful for the preparation of benzoylureas. However, such methods require high reaction temperatures and long reaction times, and produce a significant amount of undesirable by-products, thereby making them undesirable on a commercial scale.

It is therefore an object of the present invention to provide a method for the preparation of benzoylureas which uses lower reaction temperatures and shorter reaction times, and produces less undesirable by-product.

SUMMARY OF THE INVENTION

The present invention provides a method for the preparation of benzoylureas having the structural formula I

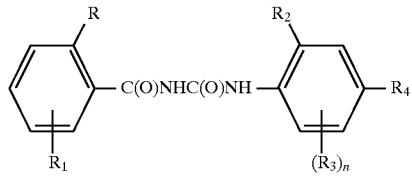

wherein

R is halogen, $C_1$–$C_4$alkyl, $C_1$–$C_4$alkoxy or $C_1$–$C_4$alkylthio;
$R_1$ is hydrogen, halogen, $C_1$–$C_4$alkyl, $C_1$–$C_4$alkoxy or $C_1$–$C_4$alkylthio;
$R_2$ is hydrogen or halogen;
$R_3$ is halogen, nitro, cyano, $C_1$–$C_4$alkyl or $C_1$–$C_4$haloalkyl;
n is an integer of 0, 1, 2 or 3;
$R_4$ is halogen or $OR_5$; and
$R_5$ is $C_1$–$C_4$haloalkyl, $C_3$–$C_7$halocycloalkyl,
  phenyl optionally substituted with up to three groups independently selected from halogen atoms, $C_1$–$C_4$haloalkyl groups, cyano groups or nitro groups, or
  2-pyridyl optionally substituted with up to three groups independently selected from halogen atoms, $C_1$–$C_4$haloalkyl groups, cyano groups or nitro groups,
which comprises reacting a substituted benzamide having the structural formula II

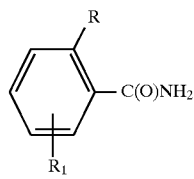

wherein R and $R_1$ are as described for formula I above with at least about one molar equivalent of a substituted phenyl isocyanate having the structural formula III

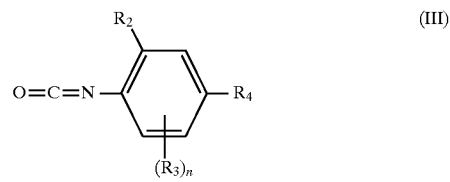

wherein $R_2$, $R_3$, $R_4$ and n are as described for formula I above, in the presence of an effective catalytic amount of a halogenating agent selected from the group consisting of N-bromosuccinimide, N-chlorosuccinimide, bromine and chlorine, hereinafter sometimes referred to as the "halogenating agent", and a base.

DETAILED DESCRIPTION OF THE INVENTION

Insects cause tremendous global economic losses by reducing crop yields and lowering crop quality. Several benzoylureas are commercially available for the control of insect species. However, the methods used to prepare benzoylureas on a commercial scale require high reaction temperatures and long reaction times, and produce a significant amount of undesirable by-products.

Advantageously, the present invention provides an improved method for the preparation of benzoylureas which uses lower reaction temperatures and shorter reaction times, and produces less undesirable by-product.

Surprisingly, it has been discovered that lower reaction temperatures and shorter reaction times are required, and less undesirable by-product is produced when N-bromosuccinimide, N-chlorosuccinimide, bromine or chlorine, and a base are used in the preparation of benzoylureas.

The effective catalytic amount of the halogenating agent is defined herein as any amount of the halogenating agent which allows the reaction to proceed at lower reaction temperatures and/or shorter reaction times compared to the reaction temperatures and reaction times when the halogenating agent is not present. Typically, this amount may be less than one molar equivalent per mole of the formula II benzamide. As it is generally not economical to use more, the effective catalytic amount of the halogenating agent is preferably about 0.001 to 0.5 molar equivalent, and more preferably about 0.01 to 0.5 molar equivalent, per mole of the formula II benzamide.

In a preferred embodiment of this invention, the base is present on a molar basis in an amount at least equal to the amount of the halogenating agent. In a more preferred embodiment of this invention, the base is present on a molar basis in an amount in excess of the amount of the halogenating agent up to about one molar equivalent of the formula II benzamide.

The desired formula I products may be isolated using standard procedures known in the art such as filtration, extraction with a suitable solvent, chromatographic separation and the like.

Bases suitable for use in the method of this invention include alkali metal hydroxides, alkaline earth metal hydroxides, tri($C_1$–$C_4$alkyl)amines, alkali metal hydrides, alkaline earth metal oxides, 1,4-diazabicyclo-[2.2.2]octane, 4-dimethylaminopyridine, potassium fluoride and the like, with sodium hydroxide, calcium oxide, 1,4-diazabicyclo[2.2.2]octane, 4-dimethylaminopyridine and potassium fluoride being preferred bases.

Preferably, the reaction is conducted in the presence of an organic solvent. Solvents suitable for use in the present invention include acetonitrile, halogenated hydrocarbon solvents such as 1,2-dichloroethane, dichloromethane, carbon tetrachloride and the like, aromatic hydrocarbon solvents such as toluene, benzene, xylene and the like, halogenated aromatic hydrocarbon solvents such as chlorobenzene, dichlorobenzene and the like, and aliphatic esters such as ethyl acetate and the like, with 1,2-dichloroethane, dichloromethane, toluene and ethyl acetate being preferred solvents.

Advantageously, the method of the present invention is preferably conducted at a temperature from about 0° C. to about 150° C., more preferably from about 0° C. up to the boiling point of the solvent employed, and still more preferably from about 10° C. to 45° C.

Preferred benzoylureas prepared by the method of the present invention are those wherein R is F, Cl or OCH$_3$;

R$_1$ is H, F, Cl or OCH$_3$;

R$_2$ is H, F or Cl;

R$_3$ is F or Cl;

n is an integer of 0, 1 or 2;

R$_4$ is F, Cl or OR$_5$; and

R$_5$ is C$_1$–C$_4$haloalkyl, phenyl substituted with one to three halogen atoms or CF$_3$ groups, or 2-pyridyl substituted with one to three halogen atoms or CF$_3$ groups.

The method of the present invention is especially useful for the preparation of benzoylureas such as N-[[[4-[2-chloro-4-(trifluoromethyl)phenoxy]-2-fluorophenyl]amino]carbonyl]-2,6-difluorobenzamide;

N-[[(3,5-dichloro-2,4-difluorophenyl)amino]carbonyl]-2,6-difluorobenzamide; and

N-[[(4-chlorophenyl)amino]carbonyl]-2,6-difluorobenzamide, among others.

In order to facilitate a further understanding of the invention, the following examples are presented. The invention should not be deemed limited by the examples as the full scope of the invention is defined in the claims.

EXAMPLE 1

Preparation of N-[[(4-chlorophenyl)amino]-carbonyl]-2,6-difluorobenzamide

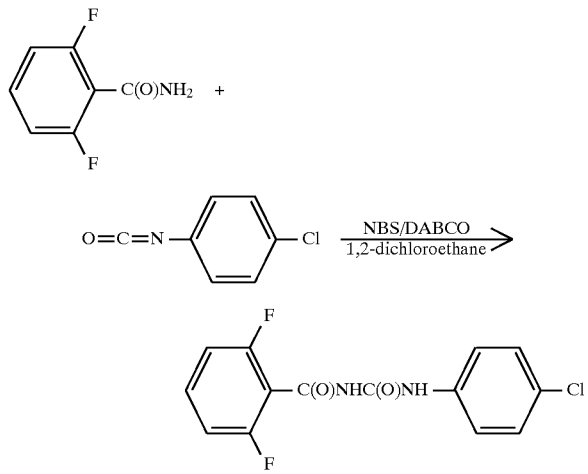

A mixture of 2,6-difluorobenzamide (1.57 g, 10.0 mmol), 4-chlorophenyl isocyanate (1.53 g, 10.0 mmol), N-bromosuccinimide (0.45 g, 2.5 mmol) and 1,4-diazabicyclo-[2.2.2]octane (0.3 g, 2.7 mmol) in 1,2-dichloroethane (25 mL) is stirred at room temperature for four hours, and diluted with water (5 mL) and methanol (15 mL). The phases are separated and the organic phase is concentrated in vacuo to obtain a solid. The solid is slurried in methanol (10 mL), separated and dried to give the title product as a solid (2.85 g, 92% yield).

Using the same amount of 2,6-difluorobenzamide and 4-chlorophenyl isocyanate (10 mmol), and using the bases, halogenating agents and solvents listed below in various amounts and combinations, N-[[(4-chlorophenyl)-amino]carbonyl]-2,6-difluorobenzamide is obtained in the yields shown in Table I.

Base
a. 1,4-diazabicyclo[2.2.2]octane
b. potassium fluoride
c. sodium hydroxide
d. calcium oxide Halogenating Agent
e. N-bromosuccinimide
f. bromine Solvent
g. 1,2-dichloroethane
h. toluene
i. acetonitrile
j. carbon tetrachloride
k. ethyl acetate

TABLE I

Percent Yields of N-[[(4-chlorophenyl)amino]carbonyl]-2,6-difluorobenzamide Under Various Conditions

| Base/mmol | Halogenating Agent/mmol | Solvent/mL | Reaction Time (hours[1]) | % Yield |
|---|---|---|---|---|
| a/8.9 | e/4.5 | g/25 | overnight | 85 |
| b/4.1 | e/2.5 | g/25 | 3 | 87 |
| c/5.0 | e/2.5 | g/25 | 4 | 85 |
| d/5.0 | e/2.5 | g/25 | 3.5 | 85 |
| a/2.7 | f/1.0 | g/25 | overnight | 53 |
| a/2.9 | e/2.5 | h/25 | 7 | 55 |
| a/4.5 | e/2.5 | g/25 | overnight | 85 |
| a/0.9 | e/0.8 | i/20 | overnight | 44 |
| a/0.9 | e/0.8 | j/20 | overnight | 30 |
| a/0.9 | e/0.8 | k/20 | overnight | 80 |

[1]Hours stirred at room temperature

What is claimed is:

1. A method for the preparation of a benzoylurea having the structural formula I

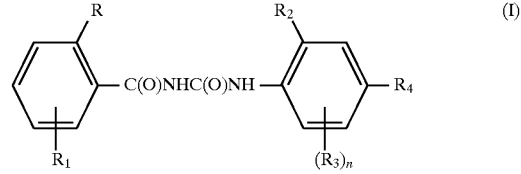

wherein

R is halogen, C$_1$–C$_4$alkyl, C$_1$–C$_4$alkoxy or C$_1$–C$_4$alkylthio;

R$_1$ is hydrogen, halogen, C$_1$–C$_4$alkyl, C$_1$–C$_4$alkoxy or C$_1$–C$_4$alkylthio;

R$_2$ is hydrogen or halogen;

R$_3$ is halogen, nitro, cyano, C$_1$–C$_4$alkyl or C$_1$–C$_4$haloalkyl;

n is an integer of 0, 1, 2 or 3;

R$_4$ is halogen or OR$_5$; and

R$_5$ is C$_1$–C$_4$haloalkyl, C$_3$–C$_7$halocycloalkyl, phenyl optionally substituted with up to three groups independently selected from halogen atoms, C$_1$–C$_4$haloalkyl groups, cyano groups or nitro groups, or 2-pyridyl optionally substituted with up to three groups independently selected from halogen atoms, $C_1$–$C_4$haloalkyl groups, cyano groups or nitro groups, which comprises reacting a substituted benzamide having the structural formula II

wherein R and $R_1$ are as described for formula I above with at least about one molar equivalent of a substituted phenyl isocyanate having the structural formula III

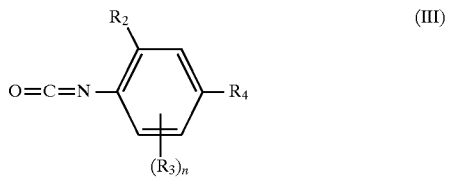

wherein $R_2$, $R_3$, $R_4$ and n are as described for formula I above, in the presence of an effective catalytic amount of a halogenating agent selected from the group consisting of N-bromosuccinimide, N-chlorosuccinimide, bromine and chlorine, and a base.

2. The method according to claim 1 wherein the halogenating agent is present in the amount of about 0.001 to 0.5 molar equivalent per mole of the formula II benzamide.

3. The method according to claim 2 wherein the halogenating agent is present in the amount of about 0.01 to 0.5 molar equivalent per mole of the formula II benzamide.

4. The method according to claim 1 wherein the base is present on a molar basis in an amount at least equal to the amount of the halogenating agent.

5. The method according to claim 4 wherein the base is present on a molar basis in an amount in excess of the amount of the halogenating agent up to about one molar equivalent of the formula II benzamide.

6. The method according to claim 1 wherein the base is selected from the group consisting of an alkali metal hydroxide, an alkaline earth metal hydroxide, a tri($C_1$-$C_4$alkyl)amine, an alkali metal hydride, an alkaline earth metal oxide, 1,4-diazabicyclo[2.2.2]octane, 4-dimethylaminopyridine, and potassium fluoride.

7. The method according to claim 6 wherein the base is selected from the group consisting of sodium hydroxide, calcium oxide, 1,4-diazabicyclo[2.2.2]octane, 4-dimethylaminopyridine, and potassium fluoride.

8. The method according to claim 1 wherein the reaction is conducted in the presence of a solvent.

9. The method according to claim 8 wherein the solvent is selected from the group consisting of a halogenated hydrocarbon, an aromatic hydrocarbon, a halogenated aromatic hydrocarbon, acetonitrile, and an aliphatic ester.

10. The method according to claim 9 wherein the solvent is selected from the group consisting of 1,2-dichloroethane, dichloromethane, toluene, and ethyl acetate.

11. The method according to claim 1 wherein the temperature of the reaction mixture is about 10° to 45° C.

12. The method according to claim 1 wherein

R is F, Cl or $OCH_3$;

$R_1$ is H, F, Cl or $OCH_3$;

$R_2$ is H, F or Cl;

$R_3$ is F or Cl;

n is an integer of 0, 1 or 2;

$R_4$ is F, Cl or $OR_5$; and $R_5$ is $C_1$–$C_4$haloalkyl, phenyl substituted with one to three halogen atoms or $CF_3$ groups, or 2-pyridyl substituted with one to three halogen atoms or $CF_3$ groups.

13. The method according to claim 12 wherein the formula I compound is selected from the group consisting of N-[[[4-[2-chloro-4-(trifluoromethyl)phenoxy]-2-fluorophenyl]amino]carbonyl]-2,6-difluorobenzamide; N-[[(3,5-dichloro-2,4-difluorophenyl)amino]carbonyl]-2,6-difluorobenzamide; and N-[[(4-chlorophenyl)amino]carbonyl]-2,6-difluorobenzamide.

* * * * *

UNITED STATES PATENT AND TRADEMARK OFFICE
CERTIFICATE OF CORRECTION

PATENT NO.  : 5,874,615
DATED       : February 23, 1999
INVENTOR(S) : Verbrugge et al It is certified that error appears in the above-identified patent and that said Letters Patent is hereby corrected as shown below:

On the title page: Item [73] Assignee: should read -- American Cyanamid Company, Madison, NJ--.

Signed and Sealed this

Eighteenth Day of July, 2000

Attest:

Q. TODD DICKINSON

*Attesting Officer*            *Director of Patents and Trademarks*